US005382686A

United States Patent [19]

Hagedorn et al.

[11] Patent Number: 5,382,686
[45] Date of Patent: Jan. 17, 1995

[54] PROCESS FOR PREPARING NITRODIPHENYL (THIO) ETHERS

[75] Inventors: Ferdinand Hagedorn; Helmut Fiege, both of Leverkusen, Germany

[73] Assignee: Bayer Aktiengesellschaft, Leverkusen, Germany

[21] Appl. No.: 70,482

[22] Filed: Jun. 2, 1993

Related U.S. Application Data

[63] Continuation of Ser. No. 762,040, Sep. 18, 1991, abandoned, which is a continuation of Ser. No. 227,859, Aug. 3, 1988, abandoned.

[30] Foreign Application Priority Data

Aug. 22, 1987 [DE] Germany .................. 3728139

[51] Int. Cl.$^6$ ........................... C07C 211/45
[52] U.S. Cl. ..................... 564/307; 564/430; 568/29; 568/38; 568/39; 568/40; 568/41; 568/56; 568/635; 568/636; 568/637; 568/639
[58] Field of Search ............. 564/307, 430; 568/29, 568/38, 39, 40, 41, 56, 635, 636, 637, 639

[56] References Cited

U.S. PATENT DOCUMENTS 4,119,629 10/1978 Miller .................... 558/411

FOREIGN PATENT DOCUMENTS 0022387 1/1981 European Pat. Off. ............ 558/411

OTHER PUBLICATIONS

*Chemical Abstracts*, vol. 98, No. 15, Apr. 11, 1983.
"Herstellung rein aromatischer Ather (Diarylather)", pp. 85–89 Sauerstoff–Verbindungen I, Teil 3, Dittus, Kroper & Meerwein (1981).
"Reaction of Aromati Compounds w/nucleo. reagents in liquid ammonia", Shtark, Kizner and Shteingarts, pp. 2051–2056, Novosibirsk Instit. of Organic Chem., Siberian Branch, Acad. of Sci. of USSR. Translated from Zhurnal Organicheskoi Khimii, vol. 18, #11, Nov. 1982.

*Primary Examiner*—Mary C. Lee
*Assistant Examiner*—Joseph K. McKane
*Attorney, Agent, or Firm*—Sprung Horn Kramer & Woods

[57] ABSTRACT

Nitrodiphenyl(thio) ethers in which the nitro group is in the ortho- or para-position with respect to the ether oxygen or ether sulphur can be prepared from halonitrobenzones in which the nitro group is in the ortho- or para-position with respect to the halogen and, alkali metal (thio)phenolates in liquid ammonia, the reaction being carried out under pressure and at a temperature from $-30°$ C. to $+140°$ C. and the ammonia being separated off after the reaction is completed.

1 Claim, No Drawings

PROCESS FOR PREPARING NITRODIPHENYL (THIO) ETHERS

This application is a continuation of application Ser. No. 762,040, filed Sep. 18, 1991, now abandoned, which is a continuation of application Ser. No. 227,859, filed Aug. 3, 1988 now abandoned.

The invention relates to a process for preparing nitrodiphenyl(thio) ethers by reaction of halonitrobenzenes and (thio)phenolates in liquid ammonia, the reaction being carried out under pressure and at a temperature from −30° C. to +140° C.; in each case, the nitro group is in the ortho- or para-position with respect to the ether oxygen or ether sulphur or with respect to the halogen.

BACKGROUND OF THE INVENTION

It is known to prepare nitrodiphenyl ethers by reaction of halonitrobenzenes with phenolates in reaction media such as, for example, chlorobenzene, phenol, dimethyl sulphoxide, sulpholane, dimethylformamide, dimethylacetamide, N-methylpyrrolidone or polyethylene glycol. In these reactions, copper is often required as a catalyst (Houben-Weyl, Methoden der organischen Chemie (Methods of Organic Chemistry), volume VI/3 (oxygen compounds I, 1965), p. 86 et seq.). Except in the case of halonitro-compounds which react particularly readily such as, for example, 2,4-dinitrochlorobenzene, fairly high reaction temperatures and long reaction times are generally required to obtain conversions of 60–79% at all. The reaction media mentioned create problems and financial expenses because they must be recovered for ecological reasons.

The preparation of nitrodiphenyl ethers has also already been attempted in the presence of liquid ammonia. At −40° C. in the presence of liquid ammonia, no reaction between para-nitrochlorobenzene and sodium phenolate was observed even after a reaction time of 10 hours; even 2,4-dinitrochlorobenzene which is much more strongly activated gave a yield of only 80%, even when the reaction was carried out with twice the molar amount of sodium phenolate in liquid ammonia at −33° C. (Zhur Org. Khim. 18 (1982), 2321–2327; English translation 1983, 2051–2056).

Surprisingly, it has now been found that nitrodiphenyl(thio) ethers can be prepared from halonitrobenzenes and (thio)phenolates in liquid ammonia at a higher temperature than hitherto expected, even though there was the risk that un der the influence of the ammonia being present at a high concentration halonitrobenzenes would carry out an aminolysis reaction to give nitroanilines. However, the reaction temperatures are considerably less than those which were hitherto thought to be necessary in the presence of the abovementioned reaction media; this is of importance especially with respect to the thermal instability of some nitro-aromatics at higher temperatures in the presence of strong bases.

The manner in which the reaction is conducted according to the invention is clearly superior even to the positive effect, mentioned in European Patent 0,022,387, of phase transfer catalysts which are stable to bases on the rate of the reaction of chloronitrobenzenes with alkali metal phenolates in the abovementioned reaction media.

SUMMARY OF THE INVENTION

The invention therefore relates to a process for preparing nitrodiphenyl(thio) ethers-of the formula

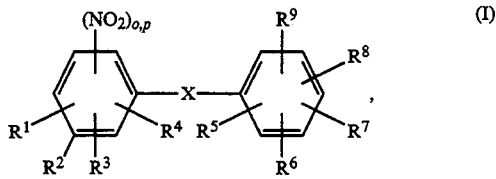

in which

X stands for oxygen or sulphur, o, p indicates the ortho- or para-position of the nitro group with respect to the ether oxygen or ether sulphur, $R^1$ and $R^2$ independently of one another denote hydrogen, halogen, nitro, cyano, alkyl, perfluoroalkyl or alkoxy, $R^3$ and $R^4$ independently of one another stand for hydrogen, halogen or alkyl, $R^5$ and $R^6$ independently of one another denote hydrogen, halogen, nitro, amino, alkyl, perfluoroalkyl, alkoxy, the carboxylic group, alkali metal carboxylate, perfluoroalkoxy or perfluoroalkylthio, $R^7$ denotes hydrogen, halogen, X-A, phenyl-X-A, alkylphenyl-X-A or $SO_2$-phenyl-X-A, in which A stands for an equivalent of an alkali metal cation or for

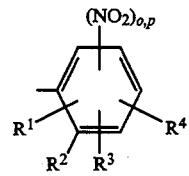

where o, p and $R^1$ to $R^4$ have the meaning mentioned and $R^8$ and $R^9$ independently of one another stand for hydrogen, halogen or alkyl and in which furthermore one of the radicals $R^3$ or $R^4$ can also stand for

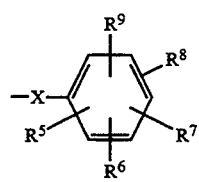

where

X and $R^5$ to $R^9$ have the meaning mentioned, whereby the carboxylic group is present as COOMe, by reacting halonitrobenzenes of the formula

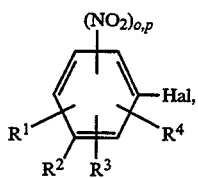

(II)

in which
o, p and $R^1$ to $R^4$ have the meaning mentioned with (thio)phenolates of the formula

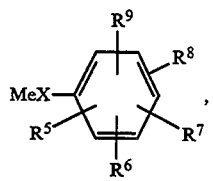

(III)

in which
Me denotes an equivalent of an alkali metal and X and $R^5$ to $R^9$ have the meaning mentioned whereby the carboxylic group is present as COOMe, in liquid ammonia, characterized in that the reaction is carried out under pressure and at a temperature from $-30°$ C. to $140°$ C., preferably from $-20°$ C. to $+130°$ C., particularly preferably from $0°$ C. to $+120°$ C., very particularly preferably from $+10°$ C. to $+110°$ C., and the ammonia is separated off by distillation after the reaction is complete.

DETAILED DESCRIPTION OF THE INVENTION

At least one nitro group is present in the nitrodiphenyl(thio) ethers which can be prepared according to the invention in the ortho- or para-position with respect to the ether oxygen or ether sulphur or in the halonitrobenzenes which serve as starting materials in the ortho- or para-position with respect to the halogen substituent which as part of the reaction according to the invention is replaced by the (thio)phenolate anion.

Examples of suitable halogens are fluorine, chlorine, bromine, preferably chlorine or bromine, particularly preferably chlorine.

Alkyl is understood to mean the straight-chain or branched radical of an aliphatic hydrocarbon preferably having 1-4 C atoms such as methyl, ethyl, propyl, isopropyl, butyl, isobutyl or tert.-butyl; particular preference is given to methyl and ethyl.

An example of a suitable perfluoroalkyl is a $C_1-C_4$-alkyl radical whose H atoms have been completely replaced by fluorine such as trifluoromethyl, perfluoroethyl, perfluoropropyl or perfluorobutyl; preference is given to trifluoromethyl.

Examples of alkoxy are the radical of a straight-chain or branched aliphatic alcohol which preferably has 1-4 C atoms such as methoxy, ethoxy, propoxy, isopropyloxy, butoxy, isobutyloxy or tert.-butoxy; preference is given to methoxy or ethoxy. The same applies to perfluoro-alkoxy and perfluoroalkylthio.

The substituent $R^7$ in the formula (I) or (III) can, in addition to other meanings, also stand for the group A bonded via an oxygen (sulphur) atom or for the group A bonded via a phenyl oxygen (sulphur) or for the group A bonded via an alkylphenyl oxygen (sulphur) or for the group A bonded via $SO_2$-phenyl-oxygen (sulphur), A either standing for an equivalent of an alkali metal cation or for the substituted nitrophenyl radical mentioned which is obtained by removal of the Hal substituent from the formula (II).

In the case where $R^7$ adopts the meanings mentioned, the (thio)phenolate (III) is equipped with a second hydroxyl or sulphydryl group (X-A) which is either present in the (thio)phenolate form like the first (thio)phenolic group X-Me or already in the etherified form; thereby the systems of dihydroxybenzenes are available such as substituted or unsubstituted resorcinol, pyrocatechol or hydroquinone, or the corresponding thio compounds.

When $R^7$ has the other meanings mentioned, polynuclear bis(thio)phenols or the monoethers thereof are obtained correspondingly. The meanings mentioned are therefore derived (in the sequence mentioned) from the systems dihydroxydiphenyl, bishydroxyphenylalkylidene compounds, such as 2,2-bishydroxyphenylpropane (bisphenol A), bishydroxyphenylmethane, 1,1-bishydroxyphenylcyclohexane and others and also from the system dihydroxydiphenylsulphone and their corresponding thio compounds.

If in such systems in the context of the formula (III) both hydroxyl groups or sulphydryl groups are present in the (thio)phenolate form, twice the amount of halonitrobenzene of the formula (II) must be used, if ether formation is to take place on both hydroxyl groups or sulphydryl groups.

Of course, it is also possible to use dihydroxy compounds or disulphydryl compounds of the type mentioned in which an ether group had already been introduced before the reaction according to the invention, that is in which A stands for the radical mentioned and which is obtained by removal of Hal to the formula (II).

What has been said before with respect of group A correspondingly also applies to the formula (I). Preferably, A in the formula (III) has the meaning of an equivalent of an alkali metal, whereas A in the formula (I) preferably stands for the substituted nitrophenyl radical which is obtained by removal of the Hal substituent from the formula (II). The same applies to $A^1$ and $A^2$ in the formulae (VI) and (VII) mentioned below.

One of the radicals $R^3$ or $R^4$ can, in addition to other meanings, also stand for the abovementioned group which is obtained by elimination of Me from the formula (III). This is the case if more than one halogen Hal in the formula (II) is activated by ortho- or para-nitro and therefore additional ether formation takes place at the position where such a further activated halogen is present. In such a case, twice the amount of (thio)phenolate of the formula (III) must be used in the reaction in a manner described above, if a second ether bond is to be formed from a second activated halogen. Preferably, the additional meaning just described for $R^3$ and $R^4$ applies to the formula (I), less preferably to the formula (II).

Me denotes an equivalent of an alkali metal, for example $Li^+$, $Na^+$, $K^+$. Preference is given to $Na^+$ and $K^+$. According to the invention, it is permitted to use mixed (thio)phenolates which contain various of the metal cations mentioned.

Preference is given to halonitrobenzenes of the formula

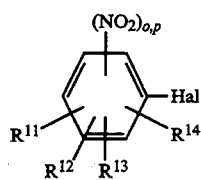

in which
- o, p indicates the ortho- or para-position of the nitro group with respect to halogen,
- $R^{11}$ denotes hydrogen, chlorine, nitro, cyano, methyl, ethyl or trifluoromethyl,
- $R^{12}$ denotes hydrogen, chlorine, bromine, methyl, ethyl, trifluoromethyl, methoxy or ethoxy and
- $R^{13}$ and $R^{14}$ independently of one another stand for hydrogen or chlorine.

Particular preference is given to chloronitrobenzenes of the formula

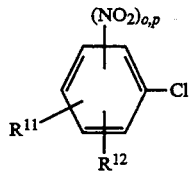

in which
- o, p indicate the ortho- or para-position of the nitro group with respect to chlorine and $R^{11}$ and $R^{12}$ have the meanings mentioned.

Preference is given to (thio)phenolates of the formula

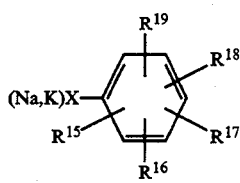

in which
- X stands for oxygen or sulphur,
- $R^{15}$ and $R^{16}$ independently of one another denote hydrogen, chlorine, bromine, nitro, amino, methyl, ethyl, trifluoromethyl, methoxy, ethoxy, the carboxylic group being present as COONs or COOK, respectively, trifluoromethoxy or trifluoromethylthio,
- $R^{17}$ denotes hydrogen, chlorine, X-$A^1$, phenyl-X-$A^1$ or alkylphenyl-X-$A^1$ and
- $R^{18}$ and $R^{19}$ independently of one another stand for hydrogen, chlorine, methyl or ethyl, where
- $A^1$ stands for Ns, K or for the radical

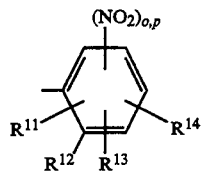

in which

- $R^{11}$ denotes hydrogen, chlorine, nitro, cyano, methyl, ethyl or trifluoromethyl,
- $R^{12}$ denotes hydrogen, chlorine, bromine, methyl, ethyl, trifluoromethyl, methoxy or ethoxy and
- $R^{13}$ and $R^{14}$ independently of one another denote hydrogen or chlorine.

Particular preference is given to (thio)phenolates of the formula

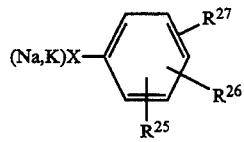

in which
- X stands for oxygen or sulphur,
- $R^{25}$ denotes hydrogen, chlorine, nitro, amino, methyl, ethyl, trifluoromethyl, methoxy, ethoxy, the carboxylic group being present as COONa or COOK, respectively, trifluoromethoxy or trifluoromethylthio,
- $R^{26}$ denotes hydrogen, chlorine, bromine, methyl, the carboxylic group being present as COONa or COOK, respectively, or trifluoromethyl and
- $R^{27}$ denotes hydrogen, chlorine or X-$A^2$, where
- $A^2$ stands for Na, K or for the radical

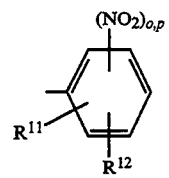

in which
- $R^{11}$ denotes hydrogen, chlorine, nitro, cyano, methyl, ethyl or trifluoromethyl and
- $R^{12}$ denotes hydrogen, chlorine, bromine, methyl, ethyl, trifluoromethyl, methoxy or ethoxy.

Very particular preference is given to (thio)phenolates of the formula

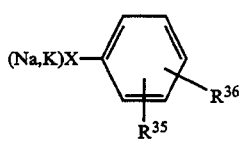

in which
- X stands for oxygen or sulphur,
- $R^{35}$ denotes hydrogen, chlorine, nitro, amino, methyl, ethyl, trifluoromethyl, methoxy, ethoxy, the carboxylic group being present as COONa or COOK, respectively, trifluoromethoxy or trifluoromethylthio and
- $R^{36}$ denotes hydrogen, chlorine, methyl, ethyl, the carboxylic group being present as COONa or COOK, respectively, or trifluoromethyl.

The reactions for (thio)ether formation which are possible according to the invention can be represented schematically by the following formula equations, the possible substitution pattern being represented globally by the unnumbered letter R.

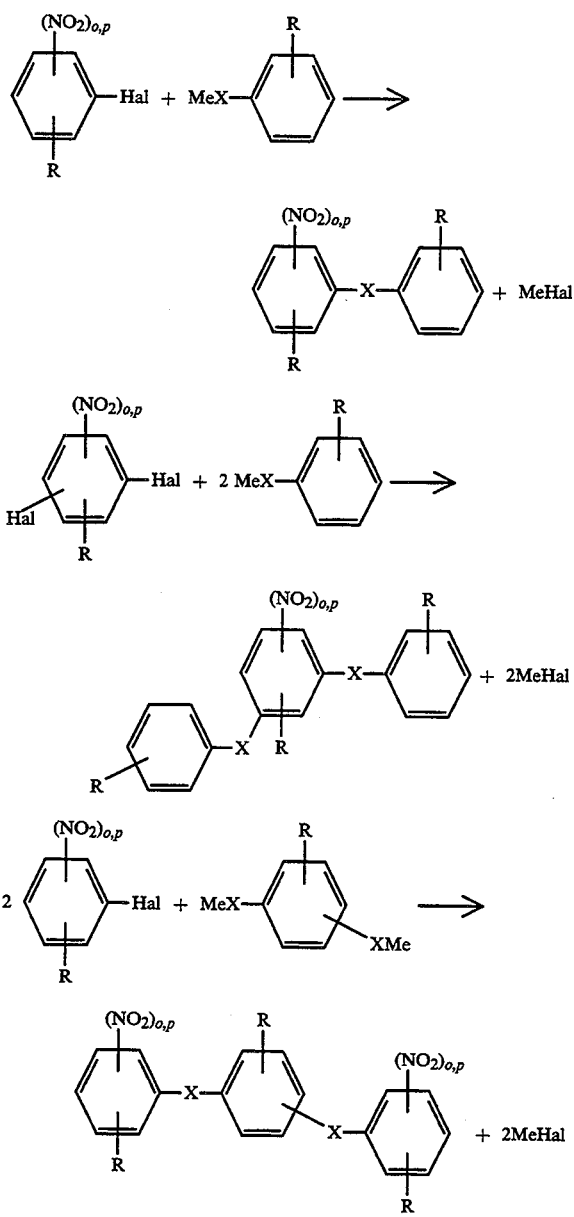

While the formation of a monoether is dealt with in the first formula equation, the second and third formula equations refer to the variations described in more detail above and in which more than one activated halogen is present in the halonitrobenzene or more than one hydroxyl group or sulphydryl group in the (thio)phenolate form is present in the (thio)phenolate to be used (in the manner also dealt with above, in a dihydroxy compound (disulphydryl compound) a hydroxyl group (sulphydryl group) can already be monoetherified in the manner also described above before entering the process according to the invention or a stepwise reaction can take place, if more than one activated halogen is present.

Examples of halonitrobenzenes which are suitable for the process according to the invention are: 2-chloronitrobenzene, 2-bromonitrobenzene, 4-fluoronitrobenzene, 4-chloronitrobenzene, 4-bromonitrobenzene, 2,3-dichloronitrobenzene, 2,4-dichloronitrobenzene, 2,5-dichloronitrobenzene, 2,6-dichloronitrobenzene, 3,4-dichloronitrobenzene, 2-chloro-3-nitrotoluene, 6-chloro-3-nitrotoluene, 1,2,4-trichloro-5-nitrobenzene, 5-chloro-2-nitroaniline, 4,6-dichloro-1,3-dinitrobenzene, 4-chloro-3-cyanonitrobenzene, 4-chloro-2-cyanonitrobenzene, 5-chloro-2-nitroaniline and 1,4-dichloro-2,5-dinitrobenzene.

Examples of (thio)phenolates which are suitable for the process according to the invention are the alkali metal salts of the following hydroxy aromatics: phenol, cresols, xylenes, nitrophenols, chlorophenols, dichlorophenols, chloronitrophenols, aminophenols, in particular meta-aminophenol, nitrocresols, hydroquinone, resorcinol, pyrocatechol, 4,4'-dihydroxydiphenyl, hexafluorobisphenol A, bisphenol A, tetramethylbisphenol A, chlorotrifluoromethylphenols, in particular 2-chloro-4-trifluoromethylphenol and 2-chloro-5-trifluoromethylphenol, 4-trifluoromethoxyphenol, 4-trifluoromethylmercaptophenol, thiophenols, mercapto and bismercapto aromatics, salicylic acid, 3-hydroxybenzoic acid, 4-hydroxybenzoic acid, 3-chloro-salicylic acid, 5-chloro-salicyclic acid, and hydroxy phthalic acids.

In the process according to the invention, a molar ratio of halonitrobenzene to (thio)phenolate group of 0.7–1.2 :1, preferably 0.9–1.05:1, particularly preferably 0.95–1:1, is established per diphenyl(thio)ether bond to be formed.

The process according to the invention is carried out at a temperature from $-30°$ C. to $+140°$ C., preferably at $-20°$ C. to $+130°$ C., particularly preferably at $0°$ C. to $+120°$ C., very particularly at preferably $+10°$ C. to $+110°$ C.

The ammonia used is maintained in the reaction system largely in the liquid phase. To this effect, a pressure is established which corresponds to the minimum vapour pressure of all components present in the reaction mixture. In addition, it is of course possible to increase the pressure by injecting nitrogen, noble gases or other gases which are inert with respect to the reaction system. However, no additional advantages are obtained thereby. Therefore, it is preferable to operate at the vapour pressure of the entire reaction system which is reached as a function of the temperature. Ammonia is used in an amount corresponding to 4–12 moles, preferably 5–10 moles, of liquid ammonia per mole of halonitrobenzene.

Under the process conditions, an inert organic solvent can be used in addition to the liquid ammonia which serves as the reaction medium. Of the many inert solvents known to one skilled in the art, preference is given to benzene, toluene, xylene, chlorobenzene, dichlorobenzene or aliphatic or cycloaliphatic hydrocarbons such as isododecane, n-pentane, n-hexane, petroleum ether of various boiling ranges or cyclohexane. Particular preference is given to benzene, toluene, xylene and aliphatic or cycloaliphatic hydrocarbons. However, preferably these solvents are only used for the purpose of the workup described below.

The liquid ammonia which serves as the reaction medium has favourable solvent properties for the substances which are to be used and are formed in the process according to the invention. This makes it possible to work at higher concentrations than was possible with the solvents used up to now. In combination with the generally shorter reaction time compared to the previous processes, significantly improved space-time yields are thereby obtained. The additional use of catalysts, for example copper or copper compounds, is omitted so that no problems concerning the disposal of heavy metal wastes arise. Liquid ammonia is a low-priced solvent which can easily be handled and recovered in industry and is, for example, cheaper than the reaction media mentioned above, namely dimethyl sulphoxide, dimethylformamide, dimethylacetamide and/or N-methylpyrrolidone, such as are used in conventional processes. Furthermore, some of these solvents are not completely stable to bases at elevated temperature and have a relatively high boiling point, making their recovery more difficult. Another point in favour of the process according to the invention which uses liquid ammonia as the reaction medium is the generally decreased reaction temperature, compared to the solvents mentioned as the reaction media.

The process according to the invention is generally carried out in such a way that the (thio)phenolate is initially introduced together with liquid ammonia in a pressure vessel, the mixture is heated to the desired temperature and the halonitrobenzene is added at this temperature at the rate at which the heat of the reaction can be removed.

In an advantageous and preferred embodiment of the process, the (thio)phenol is converted with an alkali metal hydroxide in liquid ammonia to the alkali metal phenolate and the halonitrobenzene is introduced into this mixture at the desired temperature. Hereby any carboxylic group which may be present in the (thio)phenol is converted simultaneously into alkali metal carboxylate. Therefore a sufficient amount of alkali metal hydroxide has to be charged in order to neutralize as well OH (or SH, respectively) as also COOH. The same applies in the case that a further hydroxyl or a further sulphydryl group is present in the (thio)phenolate of formula (III). If the halonitrobenzene is a liquid at this reaction temperature, it is preferably pumped into the pressure vessel in this liquid form. Furthermore, a solution or suspension of the halonitrobenzene in a solvent of the abovementioned type which is inert under the reaction conditions is also suitable for introduction into the pressure vessel. However, the starting materials ((thio)phenolates and halonitrobenzenes) can also be introduced as a mixture, liquid ammonia and further inert solvent or no solvent can then be added followed by bringing the reaction mixture to the desired reaction temperature. The variation mentioned last is recommended in the case of slowly reacting starting materials.

The preparation of the (thio)phenolates from the aromatic hydroxy compound and alkali metal hydroxide or other basic alkali metal compounds is known to one skilled in the art. In many cases, it is advantageous to form the (thio)phenolate from these materials in the reaction vessel. The small amount of reaction water does not interfere in the (thio)ether formation.

After the reaction is completed, the ammonia is separated off, for example by distillation; without further purification, it can be used for another run.

The resulting inorganic salts can be removed from the remaining reaction mixture by filtration, with or without suction or by dissolving them with water. The nitrodiphenyl(thio) ethers which are left behind are obtained in good yields and generally in remarkable purity so that in some cases an after treatment for the purpose of purification can be omitted. If small amounts of impurities are still present, they can be removed by known methods, for example by steam distillation, recrystallization or dissolution and reprecipitation or by thin-film distillation.

The workup of the reaction mixture described can also be varied in such a way that an additional solvent is used before the (complete) recovery of the ammonia by distillation. The purpose of this additional solvent is to dissolve one group of substances, either the inorganic salts or the organic components of the reaction mixture. Therefore, one of the preferred workup variations consists in adding an inert solvent of the type described above in which the alkali metal or alkaline earth metal halide formed is insoluble. The ammonia or the remaining ammonia is then removed by distillation, the inert solvent containing the dissolved organic components is freed from the salts, after which the recovery of the nitrodiphenyl(thio) ethers from the solvent phase is carried out by known methods. If such an inert organic solvent of the type mentioned had already been added for carrying out the etherification reactions further addition of such a solvent for workup can be omitted.

Another preferred variation of workup after previous addition of a solvent relates to the addition of water for dissolving the inorganic salts. In this case, too, the ammonia is subsequently removed by distillation as far as possible, the separation of the aqueous and organic phases is then carried out and the organic phase is worked up by known methods.

Examples of nitrodiphenyl(thio) ethers which can be prepared according to the invention are: 2-nitrodiphenyl ether, 4-nitrodiphenyl ether, 2-chloro-4-nitrodiphenyl ether, 4-chloro-2-nitrodiphenyl ether, 4,4'-dichloro-2-nitrodiphenyl ether, 2,4'-dichloro-4-nitrodiphenyl ether, 4'-chloro-4-nitrodiphenyl ether, 4'-chloro-2-nitrodiphenyl ether, 2'-methyl-2-nitrodiphenyl ether, 3'-amino-4-nitrodiphenyl ether, 4,4'-dinitro-2,2'-dimethyldiphenyl ether, 2-chloro-4-methyl-3'-cyano-4'-nitrodiphenyl ether, 1,4-bis-(4'-nitrophenoxy)-benzene, 5-chloro-2-nitrodiphenyl ether, 4-amino-4'-nitrodiphenyl ether, 2-cyano-4-nitrodiphenyl ether, 4-methyl-4'-nitrodiphenylthio ether, 4-trifluoromethoxy-4'-nitrodiphenyl ether, 4-trlfluoromethylthio-4'-nitrodiphenyl ether, 4-trifluoromethylthio-2'-methyl-4'-nitrodiphenyl ether, 3-(4'-nitrophenoxy)-benzoic acid and the like. It is known to a skilled artisan how to convert carboxylic groups which may be present in the nitrodiphenyl(thio) ethers into alkali metal carboxylates with the aid of alkaline reacting alkali metal compounds, and vice versa to form free carboxylic groups from carboxylates with the aid of acids.

The nitrodiphenyl(thio) ethers which can be prepared according to the invention are valuable intermediates for preparing dyestuffs, plant-protective agents or polymers. The following examples illustrate the invention without limiting it.

EXAMPLE 1

157.6 g of p-chloronitrobenzene and 116.1 g of sodium phenolate were initially introduced into a steel autoclave. At room temperature, 100 g of liquid ammonia were pumped into the pressure vessel, the mixture was heated to 70° C. and allowed to completely react with stirring over a period of 9 hours. The pressure of 28 bar initially observed dropped during the reaction to 22 bar. Removal of the ammonia by distillation and workup of the distillation residue gave 4-nitrodiphenyl ether with a yield of 213.8 g=99.4% of the theoretical yield. The product is 99.2% pure.

In comparison, this reaction in chlorobenzene as the reaction medium using a phase transfer catalyst which is stable to bases according to Example 1 of European Patent Specification 22,387 required a temperature of 130° C. giving a somewhat lower yield (95%). In the absence of the phase transfer catalyst, the yield was only 3%.

EXAMPLE 2

A steel autoclave was filled with 157.6 g of o-chloronitrobenzene and 116.1 g of sodium phenolate. At room temperature, 150 g of liquid ammonia were pumped into the vessel, the mixture was heated to 60° with stirring for 15 hours and subsequently cooled. Removal of the ammonia by distillation and workup of the distillation residue gave 202 g of 2-nitrodiphenyl ether (94% of the theoretical yield), 98.5% pure.

In comparison, the same reaction in chlorobenzene as the reaction medium instead of liquid ammonia required reaction temperatures up to 150° and a total reaction time of 90 to 100 hours to obtain the same result.

EXAMPLE 3

157.6 g of p-chloronitrobenzene and 150.5 g of sodium 4-chlorophenolate were initially introduced into a steel autoclave. At temperature, 150 g of liquid ammonia were pumped into the vessel, the mixture was brought to 80° C. and stirred at this temperature for 10 hours. 150 g of water were then pumped in the vessel, the mixture was cooled to room temperature, the pressure vessel was let down while removing the ammonia at the same time by distillation, and the reaction mixture was filtered off through a suction filter. The crystalline product was washed with water and dried to give 4-chloro-4'-nitrodiphenyl ether with a yield of 226.7 g=92.3% of the theoretical yield. The product is almost 100% pure.

EXAMPLE 4

A steel autoclave was filled with 1 mol of 3,4-dichloronitrobenzene and 117 g (1 mol) of 99.1% pure sodium phenolate, and 150 g of liquid ammonia were pumped into the vessel at room temperature. The mixture was stirred at 50° C. for 2 hours (pressure 21→18 bar). Removal of the ammonia by distillation and workup of the remaining reaction mixture gave 233.9 g of 2-chloro-4-nitrodiphenyl ether, 99.2% pure (=93.7% of the theoretical yield).

EXAMPLE 5

A steel autoclave was filled with 128.3 g (0.977 mol) of sodium 3-aminophenolate and 153.9 g (0.977 mol) of p-chloronitrobenzene. After 150 g (8.8 mol) of ammonia had been pumped into the vessel, the mixture was heated to 70° C. for 12 hours with stirring. The pressure was about 30 bar. After the reaction was completed, 200 ml of toluene were pumped into the mixture at 85° C., the mixture was cooled and the pressure vessel let down with stirring while the ammonia was removed at the same time by distillation. The toluene solution was separated from the salt by filtration with suction. Washing the salt with toluene and removing the solvent gave 3-amino-4'-nitrodiphelyl ether with a yield of 222.7 g=94.4% of the theoretical yield. The product content is 98%.

EXAMPLES 6–16

The following compounds were obtained in the same manner: 4-chloro-2-nitrodiphenyl ether, (m.p. 36°–37° C.) from 2,5-dichloronitrobenzene and sodium phenolate; 2-chloro-4'-nitrodiphenyl ether from p-chloronitrobenzene and sodium o-chlorophenolate; 4,4'-dichloro-2-nitrodiphenyl ether (m.p.: 79° C.) from 2,5-dichloronitrobenzene and sodium p-chlorophenolate; 2,4'-dichloro-4-nitrodiphenyl ether (m.p.: 107°–108° C.) from 3,4-dichloronitrobenzene and sodium p-chlorophenolate; 4'-chloro-2-nitrodiphenyl ether (m.p.: 44°–45° C.) from o-chloronitrobenzene and sodium p-chlorophenolate; 2'-methyl-2-nitrodiphenyl ether (b.p.: 194°–196°/19 mbar) from o-chloronitrobenzene and sodium 2-methylphenolate; 4,4'-dinitro-2,2'-dimethyldiphenyl ether (m.p.: 270° C.) from 3-methyl-4-chloronitrobenzene and sodium 2-methyl-4-nitrophenolate; 1,4-bis(4'-nitrophenoxy)benzene (m.p.: 232°–234° C.) from 2 mol of p-chloronitrobenzene and 1 mole of the disodium salt of p-hydroquinone; 5-chloro-2-nitrodiphenyl ether (m.p.: 85° C.) from 2,4-dichloronitrobenzene and sodium phenolate; 4-amino-4'-nitrodiphenyl ether (m.p.: 130°–131° C.) from p-nitrochlorobenzene and sodium p-aminophenolate; 2-cyano-4-nitrodiphenyl ether (m.p.: 125°–126° C.) from 2-cyano-4-nitrochlorobenzene and sodium phenolate.

EXAMPLE 17

A steel autoclave was filled with 94 g (1 mole) of phenol and 40 g of sodium hydroxide pellets (1 mole), furthermore after sealing the autoclave 150 g of ammonia were injected. At 70° C., 157.5 g (1 mole) of p-nitrochlorobenzene were pumped into the autoclave as a liquid over a period of one hour; the mixture was stirred for a further 10 hours. After the pressure vessel was let town and the product obtained was washed with water, the 4-nitrodiphenyl ether was isolated at a more than 99% purity (by gas chromatography).

EXAMPLE 18

A pressure vessel was filled with 157.5 g (1 mole) of p-nitrochlorobenzene, 116 g (1 mole) of sodium phenolate, 50 g of xylene (isomeric mixture), furthermore after the vessel was sealed 100 g of ammonia were injected. The mixture was stirred for 9 hours at 70° C. (pressure: 22 bar). After the mixture had been cooled and the pressure vessel let down, the mixture was extracted with 250 ml of water and the organic phase which was separated off was analysed. It contained 67.8% of 4-nitrodiphenyl ether, 30.6% of p-nitrochlorobenzene and 0.9% of phenol.

EXAMPLE 19

A steel autoclave was filled with 91.3 g of 2-cyano-4-nitrochlorobenzene (0.5 mol), 58 g of sodium phenolate (about 0.5 mol) and 100 g of liquid $NH_3$. The mixture was stirred for 10 hours at 16 to 18° C. (pressure: 8.8 bar). Workup of the product obtained by washing it with water and drying gave 91.2% pure 2-cyano-4-nitrodiphenyl ether (109.7 g).

EXAMPLE 20

66 g (0.5 mol) of the monosodium salt of hydroquinone, 78.5 g of p-nitrochlorobenzene and 100 g of liquid $NH_3$ were filled into a steel autoclave and heated for 6 hours at 800° C. with stirring. After the vessel had been let down and the ammonia removed, the product obtained was introduced into water and the solid was, after filtration, washed until free of salt to give 95 g, m.p. 153° to 175° C. The material consisted of 44% of 4-hydroxy-4'-nitrodiphenyl ether and 55% of 1,4-bis(4'-nitrophenoxy)benzene.

EXAMPLE 21

145 g of sodium 4-methylthiophenolate and 156.5 g of p-nitrochlorobenzene were initially introduced into a steel autoclave. 150 g of ammonia were injected, the mixture was heated to 70° C. with stirring and allowed to complete the reaction at this temperature over 6 hours. After the pressure vessel had been let down, the product been taken up in water, the salt been removed by washing and the product been dried, 241 g of 4-methyl-4'-nitrodiphenyl thioether, 99.2% pure (by gas chromatography), m.p. 80°-82° C., were obtained.

EXAMPLE 22

89.1 g of 4-trifluoromethoxyphenol (0.5 mol), 20.0 g of sodium hydroxide and 78.8 g of 4-chloronitrobenzene were initially introduced into a steel autoclave (0.7 L) and after injecting 100 g of anhydrous ammonia th mixture was heated to 80° C. for 8 hours. After the mixture had been cooled and the pressure vessel let down, the product mixture was taken up in 400 ml of methylene chloride, the undissolved material was separated off, the organic phase washed with dilute sodium hydroxide solution and water, dried and the solvent was distilled off. The initially liquid residue crystallized upon cooling and could be recrystallized from alcohol. M.p. 41.5° C. Yield: 98% of theory.

EXAMPLES 23 AND 24

The following compounds were obtained in the same manner:
4-trifluoromethylmercapto-4'-nitrodiphenyl ether, (m.p. 41°-42° C.), from sodium 4-trifluoromethylmercaptophenolate and 4-chloronitrobenzene;
4-trifluoromethylmercapto-2'-methyl-4'-nitrodiphenyl ether, (m.p. 63°-64° C.), from sodium 4-trifluoromethylmercaptophenolate and 6-chloro-3-nitrotoluene.

EXAMPLE 25

88.5 g (0.635 moles) of 3-hydroxy benzoic acid (99% pure), 100 g of p-nitrochlorebenzene, and 51,4 g sodium hydroxide (98.8% pure) were introduced into an autoclave. After removal of the air by evacuation, 150 g of ammonia were pumped into the autoclave. The mixture was stirred for 10 hours at 80° C. The initial pressure of 37 bars dropped to 34 bars during the reaction. After cooling and removal of the ammonia, the reaction product was dissolved in 800 ml of water. By acidification with hydrochloric acid the crude 3-(4'-nitrophenoxy)-benzoic acid was precipitated. Purity: 97.3%; the product could be purified by recristallization. Yield: 94%; m.p. 188° C.

What is claimed is:

1. A process for preparing 3-amino-4'-nitrodiphenyl ether, which comprises reacting p-nitrochlorobenzene with sodium-meta-aminophenolate in liquid ammonia under pressure and at a temperature of from 60° C. to 120° C., and separating off the ammonia by distillation after the reaction is completed.

* * * * *